United States Patent
Hunt et al.

(10) Patent No.: US 11,793,504 B2
(45) Date of Patent: Oct. 24, 2023

(54) SURGICAL RETRACTOR SYSTEM AND METHODS OF USE

(71) Applicant: NuVasive, Inc., San Diego, CA (US)

(72) Inventors: Leonel A. Hunt, San Diego, CA (US); Gabriel E. Hunt, San Diego, CA (US); Drew Schifle, San Diego, CA (US); Greg Causey, San Diego, CA (US); Alan Burkholder, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 7 days.

(21) Appl. No.: 17/217,602

(22) Filed: Mar. 30, 2021

(65) Prior Publication Data

US 2021/0212678 A1 Jul. 15, 2021

Related U.S. Application Data

(63) Continuation of application No. 17/179,194, filed on Feb. 18, 2021, which is a continuation of application
(Continued)

(51) Int. Cl.
*A61B 17/02* (2006.01)
*A61B 17/28* (2006.01)
*A61B 17/00* (2006.01)

(52) U.S. Cl.
CPC ........ *A61B 17/025* (2013.01); *A61B 17/0206* (2013.01); *A61B 17/282* (2013.01);
(Continued)

(58) Field of Classification Search
CPC ... A61B 17/02; A61B 17/0206; A61B 17/025; A61B 17/0256; A61B 17/0262
(Continued)

(56) References Cited

U.S. PATENT DOCUMENTS

| 186,637 A | 1/1877 | Tanner |
| 208,227 A | 9/1878 | Dorr |

(Continued)

FOREIGN PATENT DOCUMENTS

| CN | 201341901 | 11/2009 |
| EP | 303773 | 2/1989 |

(Continued)

OTHER PUBLICATIONS

International Preliminary Report on Patentability and Written Opinion for PCT/US2012/051480, ISA, dated Mar. 5, 2014.
(Continued)

*Primary Examiner* — Matthew J Lawson
(74) *Attorney, Agent, or Firm* — Seager, Tufte & Wickhem, LLP

(57) ABSTRACT

A surgical retractor includes an elongate element defining an operational axis, a first blade secured to the elongate element and comprising a blade face, a second blade moveably secured to the elongate element, wherein the second blade defines a reference point located thereon, and wherein a movement of the second blade moves the reference point in a linear direction parallel to the operational axis and orthogonal to the blade face. A guide element may be removably located within an opening located on either the first blade or the second blade.

18 Claims, 9 Drawing Sheets

Related U.S. Application Data

No. 16/237,247, filed on Dec. 31, 2018, now Pat. No. 10,952,715, which is a continuation of application No. 14/239,528, filed as application No. PCT/US2012/051480 on Aug. 17, 2012, now Pat. No. 10,166,018.

(60) Provisional application No. 61/532,751, filed on Sep. 9, 2011, provisional application No. 61/525,646, filed on Aug. 19, 2011.

(52) U.S. Cl.
CPC ............... *A61B 2017/0092* (2013.01); *A61B 2017/00915* (2013.01); *A61B 2017/0256* (2013.01); *F04C 2270/0421* (2013.01)

(58) Field of Classification Search
USPC .................... 600/214, 219, 221, 222, 228
See application file for complete search history.

(56) References Cited

U.S. PATENT DOCUMENTS

| | | |
|---|---|---|
| 245,789 A | 8/1881 | Clould |
| 295,445 A | 3/1884 | Shivler |
| 300,561 A | 6/1884 | Birdsall |
| 340,521 A | 4/1886 | Priestly |
| 369,860 A | 9/1887 | Kempster |
| 972,983 A | 10/1910 | Arthur |
| 1,003,232 A | 9/1911 | Cerbo |
| 1,044,348 A | 11/1912 | Cerbo |
| 1,223,812 A | 4/1917 | Listiak |
| 1,328,624 A | 1/1920 | Graham |
| 1,456,116 A | 5/1923 | Bessesen |
| 1,548,184 A | 8/1925 | Cameron |
| 1,919,120 A | 7/1933 | O'Connor et al. |
| 2,594,086 A | 4/1952 | Smith |
| 2,704,064 A | 3/1955 | Fizzell et al. |
| 2,736,002 A | 2/1956 | Oriel |
| 2,807,259 A | 9/1957 | Guerriero |
| 2,808,826 A | 10/1957 | Reiner et al. |
| 3,030,948 A | 4/1962 | Loeffler |
| 3,364,929 A | 1/1968 | Ide et al. |
| 3,384,077 A | 5/1968 | Gauthier |
| 3,509,873 A | 5/1970 | Karlin et al. |
| 3,522,799 A | 8/1970 | Gauthier |
| 3,664,329 A | 5/1972 | Naylor |
| 3,682,162 A | 8/1972 | Colyer |
| 3,724,449 A | 4/1973 | Gauthier |
| 3,749,088 A | 7/1973 | Kohlmann |
| 3,785,368 A | 1/1974 | McCarthy et al. |
| 3,803,716 A | 4/1974 | Garnier |
| 3,830,226 A | 8/1974 | Staub et al. |
| 3,957,036 A | 5/1976 | Normann |
| 3,965,890 A | 6/1976 | Gauthier |
| 4,024,859 A | 5/1977 | Slepyan et al. |
| 4,099,519 A | 7/1978 | Warren |
| 4,116,232 A | 9/1978 | Rabban |
| 4,151,837 A | 5/1979 | Millard, Jr. et al. |
| 4,156,424 A | 5/1979 | Burgin |
| 4,164,214 A | 8/1979 | Stark et al. |
| 4,165,746 A | 8/1979 | Burgin |
| 4,207,897 A | 6/1980 | Lloyd et al. |
| 4,224,949 A | 9/1980 | Scott et al. |
| 4,226,228 A | 10/1980 | Shin et al. |
| 4,226,288 A | 10/1980 | Collins, Jr. |
| 4,235,242 A | 11/1980 | Howson et al. |
| 4,285,347 A | 8/1981 | Hess |
| 4,291,705 A | 9/1981 | Severinghaus et al. |
| 4,449,532 A | 5/1984 | Storz |
| 4,457,300 A | 7/1984 | Budde |
| 4,461,284 A | 7/1984 | Fackler |
| 4,461,300 A | 7/1984 | Christensen |
| 4,512,351 A | 4/1985 | Pohndorf |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,013 A | 6/1986 | Jones et al. |
| 4,595,018 A | 6/1986 | Rantala |
| 4,611,597 A | 9/1986 | Kraus |
| 4,616,635 A | 10/1986 | Caspar et al. |
| 4,633,889 A | 1/1987 | Talalla et al. |
| 4,658,835 A | 4/1987 | Pohndorf |
| 4,686,972 A | 8/1987 | Kurland |
| 4,702,230 A | 10/1987 | Pelta |
| 4,744,371 A | 5/1988 | Harris |
| 4,747,394 A | 5/1988 | Watanabe |
| 4,747,395 A | 5/1988 | Brief |
| 4,753,223 A | 6/1988 | Bremer |
| 4,759,377 A | 7/1988 | Dykstra |
| 4,784,150 A | 11/1988 | Voorhies et al. |
| 4,807,642 A | 2/1989 | Brown |
| 4,817,587 A | 4/1989 | Janese |
| 4,829,985 A | 5/1989 | Couetil |
| 4,852,552 A | 8/1989 | Chaux |
| 4,881,525 A | 11/1989 | Williams |
| 4,892,105 A | 1/1990 | Prass |
| 4,913,134 A | 4/1990 | Luque |
| 4,917,274 A | 4/1990 | Asa et al. |
| 4,917,704 A | 4/1990 | Frey et al. |
| 4,926,865 A | 5/1990 | Oman |
| 4,934,352 A | 6/1990 | Sullivan, Jr. |
| 4,950,257 A | 8/1990 | Hibbs et al. |
| 4,962,766 A | 10/1990 | Hierzon |
| 4,964,411 A | 10/1990 | Johnson et al. |
| 5,007,902 A | 4/1991 | Witt |
| 5,015,247 A | 5/1991 | Michelson |
| 5,045,054 A | 9/1991 | Hood et al. |
| 5,052,373 A | 10/1991 | Michelson |
| 5,058,602 A | 10/1991 | Brody |
| 5,081,990 A | 1/1992 | Deletis |
| 5,092,344 A | 3/1992 | Lee |
| 5,127,403 A | 7/1992 | Brownlee |
| 5,161,533 A | 11/1992 | Prass et al. |
| 5,171,279 A | 12/1992 | Mathews |
| 5,192,327 A | 3/1993 | Brantigan |
| 5,195,541 A | 3/1993 | Obenchain |
| 5,196,015 A | 3/1993 | Neubardt |
| 5,215,100 A | 6/1993 | Spitz et al. |
| RE34,390 E | 9/1993 | Culver |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,295,994 A | 3/1994 | Bonutti |
| 5,299,563 A | 4/1994 | Seton |
| 5,312,417 A | 5/1994 | Wilk |
| 5,313,956 A | 5/1994 | Knutsson et al. |
| 5,313,962 A | 5/1994 | Obenchain |
| 5,327,902 A | 7/1994 | Lemmen |
| 5,331,975 A | 7/1994 | Bonutti |
| 5,333,618 A | 8/1994 | Lekhtman et al. |
| 5,342,384 A | 8/1994 | Sugarbaker |
| 5,357,983 A | 10/1994 | Mathews |
| 5,375,067 A | 12/1994 | Berchin |
| 5,375,594 A | 12/1994 | Cueva |
| 5,383,876 A | 1/1995 | Nardella |
| 5,395,317 A | 3/1995 | Kambin |
| 5,450,845 A | 9/1995 | Axelgaard |
| 5,468,241 A | 11/1995 | Metz-Stavenhagen et al. |
| 5,472,426 A | 12/1995 | Bonati et al. |
| 5,474,057 A | 12/1995 | Makower et al. |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,487,739 A | 1/1996 | Aebischer et al. |
| 5,509,893 A | 4/1996 | Pracas |
| 5,512,038 A | 4/1996 | O'Neal et al. |
| 5,514,153 A | 5/1996 | Bonutti |

(56) References Cited

U.S. PATENT DOCUMENTS

| | | |
|---|---|---|
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,569,290 A | 10/1996 | McAfee |
| 5,571,149 A | 11/1996 | Liss et al. |
| 5,579,781 A | 12/1996 | Cooke |
| 5,593,429 A | 1/1997 | Ruff |
| 5,599,279 A | 2/1997 | Slotman et al. |
| 5,630,813 A | 5/1997 | Kieturakis |
| 5,667,508 A | 9/1997 | Errico et al. |
| 5,671,752 A | 9/1997 | Sinderby et al. |
| 5,681,265 A | 10/1997 | Maeda et al. |
| 5,688,223 A | 11/1997 | Rosendahl |
| 5,707,359 A | 1/1998 | Bufalini |
| 5,711,307 A | 1/1998 | Smits |
| 5,728,046 A | 3/1998 | Mayer et al. |
| 5,733,290 A | 3/1998 | McCue et al. |
| 5,741,253 A | 4/1998 | Michelson |
| 5,741,261 A | 4/1998 | Moskovitz et al. |
| 5,759,159 A | 6/1998 | Masreliez |
| 5,762,629 A | 6/1998 | Kambin |
| 5,772,583 A | 6/1998 | Wright et al. |
| 5,772,661 A | 6/1998 | Michelson |
| 5,775,331 A | 7/1998 | Raymond et al. |
| 5,776,144 A | 7/1998 | Leysieffer et al. |
| 5,779,642 A | 7/1998 | Nightengale |
| 5,785,658 A | 7/1998 | Benaron et al. |
| 5,792,044 A | 8/1998 | Foley et al. |
| 5,795,291 A | 8/1998 | Koros et al. |
| 5,797,854 A | 8/1998 | Hedgecock |
| 5,797,909 A | 8/1998 | Michelson |
| 5,814,073 A | 9/1998 | Bonutti |
| 5,830,151 A | 11/1998 | Hadzic et al. |
| 5,846,192 A | 12/1998 | Teixido |
| 5,851,191 A | 12/1998 | Gozani |
| 5,853,373 A | 12/1998 | Griffith et al. |
| 5,860,973 A | 1/1999 | Michelson |
| 5,862,314 A | 1/1999 | Jeddeloh |
| 5,865,730 A | 2/1999 | Fox et al. |
| 5,872,314 A | 2/1999 | Clinton |
| 5,882,298 A | 3/1999 | Sharratt |
| 5,885,210 A | 3/1999 | Cox |
| 5,885,219 A | 3/1999 | Nightengale |
| 5,888,196 A | 3/1999 | Bonutti |
| 5,891,147 A | 4/1999 | Moskovitz et al. |
| 5,893,831 A | 4/1999 | Koros et al. |
| 5,902,231 A | 5/1999 | Foley et al. |
| 5,902,233 A | 5/1999 | Farley et al. |
| 5,928,139 A | 7/1999 | Koros et al. |
| 5,928,158 A | 7/1999 | Aristides |
| 5,931,777 A | 8/1999 | Sava |
| 5,935,131 A | 8/1999 | Bonutti |
| 5,944,658 A | 8/1999 | Koros et al. |
| 5,967,974 A | 10/1999 | Nicholas et al. |
| 5,976,094 A | 11/1999 | Gozani |
| 5,984,865 A | 11/1999 | Farley et al. |
| 5,993,385 A | 11/1999 | Johnston et al. |
| 6,004,262 A | 12/1999 | Putz et al. |
| 6,004,312 A | 12/1999 | Finneran et al. |
| 6,007,487 A | 12/1999 | Foley et al. |
| 6,010,520 A | 1/2000 | Pattison |
| 6,024,696 A | 2/2000 | Hoftman et al. |
| 6,024,697 A | 2/2000 | Pisarik |
| 6,027,456 A | 2/2000 | Feler et al. |
| 6,038,469 A | 3/2000 | Karlsson et al. |
| 6,038,477 A | 3/2000 | Kayyali |
| 6,042,540 A | 3/2000 | Johnston et al. |
| 6,042,542 A | 3/2000 | Koros et al. |
| 6,050,992 A | 4/2000 | Nichols |
| 6,074,343 A | 6/2000 | Nathanson et al. |
| 6,080,105 A | 6/2000 | Spears |
| 6,083,154 A | 7/2000 | Liu et al. |
| 6,095,987 A | 8/2000 | Shmulewitz et al. |
| 6,104,957 A | 8/2000 | Alo et al. |
| 6,104,960 A | 8/2000 | Duysens et al. |
| 6,120,503 A | 9/2000 | Michelson |
| 6,126,660 A | 10/2000 | Dietz |
| 6,132,386 A | 10/2000 | Gozani et al. |
| 6,132,387 A | 10/2000 | Gozani et al. |
| 6,135,965 A | 10/2000 | Tumer et al. |
| 6,139,493 A | 10/2000 | Koros et al. |
| 6,146,335 A | 11/2000 | Gozani |
| 6,152,871 A | 11/2000 | Foley et al. |
| 6,159,179 A | 12/2000 | Simonson |
| 6,161,047 A | 12/2000 | King et al. |
| 6,174,311 B1 | 1/2001 | Branch |
| 6,181,961 B1 | 1/2001 | Prass |
| 6,196,969 B1 | 3/2001 | Bester et al. |
| 6,200,263 B1 | 3/2001 | Person |
| 6,206,826 B1 | 3/2001 | Mathews et al. |
| 6,206,828 B1 | 3/2001 | Wright |
| 6,213,941 B1 | 4/2001 | Benetti et al. |
| 6,217,509 B1 | 4/2001 | Foley et al. |
| 6,224,545 B1 | 5/2001 | Cocchia et al. |
| 6,224,549 B1 | 5/2001 | Drongelen |
| 6,234,961 B1 | 5/2001 | Gray |
| 6,241,729 B1 | 6/2001 | Estes |
| 6,245,082 B1 | 6/2001 | Gellman et al. |
| 6,259,945 B1 | 7/2001 | Epstein et al. |
| 6,264,396 B1 | 7/2001 | Dobrovolny |
| 6,264,651 B1 | 7/2001 | Underwood et al. |
| 6,266,558 B1 | 7/2001 | Gozani et al. |
| 6,273,905 B1 | 8/2001 | Streeter |
| 6,292,701 B1 | 9/2001 | Prass et al. |
| 6,296,609 B1 | 10/2001 | Brau |
| 6,306,100 B1 | 10/2001 | Prass |
| 6,308,712 B1 | 10/2001 | Shaw |
| 6,312,392 B1 | 11/2001 | Herzon |
| 6,322,500 B1 | 11/2001 | Sikora et al. |
| 6,325,764 B1 | 12/2001 | Griffith et al. |
| 6,334,068 B1 | 12/2001 | Hacker |
| 6,340,345 B1 | 1/2002 | Lees et al. |
| 6,348,058 B1 | 2/2002 | Melkent et al. |
| 6,360,750 B1 | 3/2002 | Gerber et al. |
| 6,371,968 B1 | 4/2002 | Kogasaka et al. |
| 6,395,007 B1 | 5/2002 | Bhatnagar et al. |
| 6,416,465 B2 | 7/2002 | Brau |
| 6,425,859 B1 | 7/2002 | Foley et al. |
| 6,425,887 B1 | 7/2002 | McGuckin et al. |
| 6,425,901 B1 | 7/2002 | Zhu et al. |
| 6,450,952 B1 | 9/2002 | Rioux et al. |
| 6,451,015 B1 | 9/2002 | Rittman, III et al. |
| 6,466,817 B1 | 10/2002 | Kaula et al. |
| 6,468,205 B1 | 10/2002 | Mollenauer |
| 6,468,207 B1 | 10/2002 | Fowler, Jr. |
| 6,500,116 B1 | 12/2002 | Knapp |
| 6,500,128 B2 | 12/2002 | Marino |
| 6,506,151 B2 | 1/2003 | Estes et al. |
| 6,520,907 B1 | 2/2003 | Foley et al. |
| 6,524,238 B2 | 2/2003 | Velikaris et al. |
| 6,524,320 B2 | 2/2003 | DiPoto |
| 6,535,759 B1 | 3/2003 | Epstein et al. |
| 6,564,078 B1 | 5/2003 | Marino et al. |
| 6,579,244 B2 | 6/2003 | Goodwin |
| 6,599,294 B2 | 7/2003 | Fuss et al. |
| 6,602,190 B2 | 8/2003 | Dobrovolny |
| 6,620,157 B1 | 9/2003 | Dabney et al. |
| 6,645,194 B2 | 11/2003 | Briscoe et al. |
| 6,648,818 B2 | 11/2003 | Cartier et al. |
| 6,679,833 B2 | 1/2004 | Smith et al. |
| 6,685,632 B1 | 2/2004 | Hu et al. |
| 6,692,434 B2 | 2/2004 | Ritland |
| 6,719,692 B2 | 4/2004 | Kleffner et al. |
| 6,733,444 B2 | 5/2004 | Phillips |
| 6,760,616 B2 | 7/2004 | Hoey et al. |
| 6,770,074 B2 | 8/2004 | Michelson |
| 6,796,985 B2 | 9/2004 | Bolger et al. |
| 6,810,281 B2 | 10/2004 | Brock et al. |
| 6,819,956 B2 | 11/2004 | DiLorenzo |
| 6,829,508 B2 | 12/2004 | Schulman et al. |
| 6,847,849 B2 | 1/2005 | Mamo et al. |
| 6,849,047 B2 | 2/2005 | Goodwin |
| 6,855,105 B2 | 2/2005 | Jackson, III |

(56) References Cited

U.S. PATENT DOCUMENTS

| | | |
|---|---|---|
| 6,860,850 B2 | 3/2005 | Phillips et al. |
| 6,869,398 B2 | 3/2005 | Obenchain |
| 6,871,099 B1 | 3/2005 | Whitehurst et al. |
| 6,887,197 B2 | 5/2005 | Phillips |
| 6,887,198 B2 | 5/2005 | Phillips et al. |
| 6,902,569 B2 | 6/2005 | Parmer et al. |
| 6,916,330 B2 | 7/2005 | Simonson |
| 6,926,728 B2 | 8/2005 | Zucherman et al. |
| 6,929,606 B2 | 8/2005 | Ritland |
| 6,945,933 B2 | 9/2005 | Branch et al. |
| 6,951,538 B2 | 10/2005 | Ritland |
| 7,001,333 B2 | 2/2006 | Hamel et al. |
| 7,014,609 B2 | 3/2006 | Cartier et al. |
| 7,029,472 B1 | 4/2006 | Fortin |
| 7,047,082 B1 | 5/2006 | Schrom et al. |
| 7,050,848 B2 | 5/2006 | Hoey et al. |
| 7,056,287 B2 | 6/2006 | Taylor et al. |
| 7,079,883 B2 | 7/2006 | Marino et al. |
| 7,089,059 B1 | 8/2006 | Pless |
| 7,108,698 B2 | 9/2006 | Robbins et al. |
| 7,147,599 B2 | 12/2006 | Phillips et al. |
| 7,166,073 B2 | 1/2007 | Ritland |
| 7,177,677 B2 | 2/2007 | Kaula et al. |
| 7,182,729 B2 | 2/2007 | Abdelgany et al. |
| 7,182,731 B2 | 2/2007 | Nguyen et al. |
| 7,198,598 B2 | 4/2007 | Smith et al. |
| 7,207,949 B2 | 4/2007 | Miles et al. |
| 7,214,186 B2 | 5/2007 | Ritland |
| 7,226,451 B2 | 6/2007 | Shluzas et al. |
| 7,235,048 B2 | 6/2007 | Rein et al. |
| 7,261,688 B2 | 8/2007 | Smith et al. |
| 7,294,104 B2 | 11/2007 | Person |
| 7,374,534 B2 | 5/2008 | Dalton |
| 7,396,328 B2 | 7/2008 | Penenberg |
| 7,455,639 B2 | 11/2008 | Ritland |
| 7,470,236 B1 | 12/2008 | Kelleher et al. |
| 7,473,222 B2 | 1/2009 | Dewey et al. |
| 7,473,223 B2 | 1/2009 | Fetzer |
| 7,473,269 B1 | 1/2009 | Hynes |
| 7,481,766 B2 | 1/2009 | Lee et al. |
| 7,522,953 B2 | 4/2009 | Kaula et al. |
| 7,537,565 B2 | 5/2009 | Bass |
| 7,556,601 B2 | 7/2009 | Branch et al. |
| 7,569,014 B2 | 8/2009 | Bass et al. |
| 7,582,058 B1 | 9/2009 | Miles et al. |
| 7,588,537 B2 | 9/2009 | Bass |
| 7,643,884 B2 | 1/2010 | Pond et al. |
| 7,654,954 B1 | 2/2010 | Phillips et al. |
| 7,691,057 B2 | 4/2010 | Miles et al. |
| 7,693,562 B2 | 4/2010 | Marino et al. |
| 7,717,959 B2 | 5/2010 | William et al. |
| 7,722,618 B2 | 5/2010 | Estes et al. |
| 7,744,530 B2 | 6/2010 | Person |
| 7,753,844 B2 | 7/2010 | Sharratt et al. |
| 7,758,501 B2 | 7/2010 | Frasier et al. |
| 7,819,801 B2 | 10/2010 | Miles et al. |
| 7,850,608 B2 | 12/2010 | Hamada |
| 7,905,840 B2 | 3/2011 | Pimenta et al. |
| 7,909,829 B2 | 3/2011 | Patel et al. |
| 7,909,848 B2 | 3/2011 | Patel et al. |
| 7,927,337 B2 | 4/2011 | Keller |
| 7,931,589 B2 | 4/2011 | Cohen et al. |
| 7,935,051 B2 | 5/2011 | Miles |
| 7,935,053 B2 | 5/2011 | Karpowicz et al. |
| 7,946,982 B2 | 5/2011 | Hamada |
| 7,959,564 B2 | 6/2011 | Ritland |
| 7,981,031 B2 | 7/2011 | Frasier et al. |
| 8,000,782 B2 | 8/2011 | Gharib et al. |
| 8,005,535 B2 | 8/2011 | Gharib et al. |
| 8,021,430 B2 | 9/2011 | Michelson |
| 8,062,217 B2 | 11/2011 | Boucher et al. |
| 8,066,710 B2 | 11/2011 | Estes et al. |
| 8,133,173 B2 | 3/2012 | Miles et al. |
| 8,137,284 B2 | 3/2012 | Miles et al. |
| 8,182,423 B2 | 5/2012 | Miles |
| 8,192,356 B2 | 6/2012 | Miles |
| 8,251,997 B2 | 8/2012 | Michelson |
| 8,303,458 B2 | 11/2012 | Fukano et al. |
| 8,313,430 B1 | 11/2012 | Pimenta |
| 8,343,046 B2 | 1/2013 | Miles et al. |
| 8,343,224 B2 | 1/2013 | Lynn et al. |
| 8,388,527 B2 | 3/2013 | Miles et al. |
| 8,449,463 B2 | 5/2013 | Nunley et al. |
| 8,636,655 B1 | 1/2014 | Childs |
| 9,486,133 B2 | 11/2016 | Lee et al. |
| 2001/0037123 A1 | 11/2001 | Hancock |
| 2001/0039949 A1 | 11/2001 | Loubser |
| 2001/0056280 A1 | 12/2001 | Underwood et al. |
| 2002/0007129 A1 | 1/2002 | Marino |
| 2002/0010392 A1 | 1/2002 | Desai |
| 2002/0072686 A1 | 6/2002 | Hoey et al. |
| 2002/0077531 A1 | 6/2002 | Puchovsky et al. |
| 2002/0077632 A1 | 6/2002 | Tsou |
| 2002/0123744 A1 | 9/2002 | Reynard |
| 2002/0123780 A1 | 9/2002 | Grill et al. |
| 2002/0147387 A1 | 10/2002 | Paolitto et al. |
| 2002/0161415 A1 | 10/2002 | Cohen et al. |
| 2002/0193843 A1 | 12/2002 | Hill et al. |
| 2003/0032966 A1 | 2/2003 | Foley et al. |
| 2003/0060686 A1 | 3/2003 | Taylor et al. |
| 2003/0070682 A1 | 4/2003 | Wilson et al. |
| 2003/0083688 A1 | 5/2003 | Simonson |
| 2003/0105503 A1 | 6/2003 | Marino |
| 2003/0139648 A1 | 7/2003 | Foley et al. |
| 2003/0149341 A1 | 8/2003 | Clifton |
| 2003/0225405 A1 | 12/2003 | Weiner |
| 2003/0229353 A1 | 12/2003 | Cragg |
| 2003/0236544 A1 | 12/2003 | Lunsford et al. |
| 2004/0176665 A1* | 9/2004 | Branch ............ A61B 17/0206 600/210 |
| 2004/0199084 A1 | 10/2004 | Kelleher et al. |
| 2004/0225228 A1 | 11/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0075578 A1 | 4/2005 | Gharib et al. |
| 2005/0080320 A1* | 4/2005 | Lee ............ A61B 17/0293 600/214 |
| 2005/0149035 A1 | 7/2005 | Pimenta et al. |
| 2005/0182454 A1 | 8/2005 | Gharib et al. |
| 2005/0192486 A1 | 9/2005 | Hamel et al. |
| 2005/0192575 A1 | 9/2005 | Pacheco |
| 2005/0240081 A1 | 10/2005 | Eliachar |
| 2005/0277812 A1 | 12/2005 | Myles |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0178693 A1 | 8/2006 | Hamada |
| 2006/0181048 A1 | 8/2006 | Stowell et al. |
| 2006/0183978 A1 | 8/2006 | Howard |
| 2006/0206009 A1 | 9/2006 | Von Wald et al. |
| 2006/0224078 A1 | 10/2006 | Hoey et al. |
| 2007/0016097 A1 | 1/2007 | Farquhar et al. |
| 2007/0038033 A1 | 2/2007 | Jones et al. |
| 2007/0038216 A1 | 2/2007 | Hamada |
| 2007/0073112 A1 | 3/2007 | Holmes |
| 2007/0083086 A1 | 4/2007 | LeVahn et al. |
| 2007/0129608 A1 | 6/2007 | Sandhu |
| 2007/0198062 A1 | 8/2007 | Miles et al. |
| 2007/0208227 A1* | 9/2007 | Smith ............ A61B 5/389 600/219 |
| 2007/0208228 A1 | 9/2007 | Pavento et al. |
| 2007/0238932 A1* | 10/2007 | Jones ............ A61B 17/02 600/224 |
| 2007/0293782 A1 | 12/2007 | Marino |
| 2008/0058606 A1 | 3/2008 | Miles et al. |
| 2008/0058838 A1 | 3/2008 | Steinberg |
| 2008/0064976 A1 | 3/2008 | Kelleher et al. |
| 2008/0064977 A1 | 3/2008 | Kelleher et al. |
| 2008/0065144 A1 | 3/2008 | Marino et al. |
| 2008/0065178 A1 | 3/2008 | Kelleher et al. |
| 2008/0071145 A1 | 3/2008 | Bjork et al. |
| 2008/0071191 A1 | 3/2008 | Kelleher et al. |
| 2008/0097164 A1 | 4/2008 | Miles et al. |

(56) References Cited

U.S. PATENT DOCUMENTS

| | | |
|---|---|---|
| 2008/0114208 A1 | 5/2008 | Hutton |
| 2008/0132764 A1 | 6/2008 | Hamada |
| 2008/0146881 A1 | 6/2008 | Alimi et al. |
| 2008/0146885 A1 | 6/2008 | Protopsaltis |
| 2008/0221394 A1 | 9/2008 | Melkent et al. |
| 2008/0249372 A1 | 10/2008 | Reglos et al. |
| 2008/0300465 A1 | 12/2008 | Feigenwinter et al. |
| 2009/0012370 A1 | 1/2009 | Gutierrez et al. |
| 2009/0012527 A1 | 1/2009 | Mignucci et al. |
| 2009/0036746 A1* | 2/2009 | Blackwell .......... A61B 17/0206 600/219 |
| 2009/0076333 A1 | 3/2009 | Bjork |
| 2009/0076516 A1 | 3/2009 | Lowry et al. |
| 2009/0105547 A1 | 4/2009 | Vayser et al. |
| 2009/0124860 A1 | 5/2009 | Miles et al. |
| 2009/0124861 A1 | 5/2009 | Fetzer |
| 2009/0138050 A1 | 5/2009 | Ferree |
| 2009/0192403 A1 | 7/2009 | Gharib et al. |
| 2009/0203967 A1 | 8/2009 | Branch et al. |
| 2009/0204016 A1 | 8/2009 | Gharib et al. |
| 2009/0227845 A1 | 9/2009 | Lo et al. |
| 2009/0306480 A1* | 12/2009 | Protopsaltis ....... A61B 17/0206 600/219 |
| 2010/0069783 A1 | 3/2010 | Miles et al. |
| 2010/0081885 A1 | 4/2010 | Wing et al. |
| 2010/0113885 A1 | 5/2010 | Mcbride et al. |
| 2010/0130827 A1 | 5/2010 | Pimenta et al. |
| 2010/0152603 A1 | 6/2010 | Miles et al. |
| 2010/0160738 A1 | 6/2010 | Miles et al. |
| 2010/0174146 A1 | 7/2010 | Miles et al. |
| 2010/0174148 A1 | 7/2010 | Miles et al. |
| 2010/0217089 A1 | 8/2010 | Farley et al. |
| 2010/0256454 A1 | 10/2010 | Farley |
| 2010/0298647 A1 | 11/2010 | Black et al. |
| 2010/0298648 A1 | 11/2010 | Gray |
| 2010/0312068 A1 | 12/2010 | Dalton |
| 2011/0004067 A1 | 1/2011 | Marchek et al. |
| 2011/0034781 A1 | 2/2011 | Loftus et al. |
| 2011/0046448 A1 | 2/2011 | Paolitto et al. |
| 2011/0130793 A1 | 6/2011 | Woolley et al. |
| 2011/0137130 A1 | 6/2011 | Thalgott et al. |
| 2011/0144450 A1 | 6/2011 | Paolitto et al. |
| 2011/0172494 A1 | 7/2011 | Bass et al. |
| 2011/0190588 A1 | 8/2011 | McKay |
| 2011/0201897 A1 | 8/2011 | Bertagnoli et al. |
| 2011/0208008 A1 | 8/2011 | Michaeli et al. |
| 2011/0224497 A1 | 9/2011 | Weiman et al. |
| 2011/0245836 A1 | 10/2011 | Hamada |
| 2011/0257487 A1 | 10/2011 | Thalgott et al. |
| 2011/0301423 A1 | 12/2011 | Koros et al. |
| 2011/0313530 A1 | 12/2011 | Gharib et al. |
| 2012/0016422 A1 | 1/2012 | Hua |
| 2012/0022335 A1 | 1/2012 | Assaker |
| 2012/0083662 A1 | 4/2012 | Hamada et al. |
| 2012/0130180 A1 | 5/2012 | Pell et al. |
| 2012/0172670 A1 | 7/2012 | Hamada |
| 2012/0197300 A1 | 8/2012 | Loftus et al. |
| 2012/0238822 A1 | 9/2012 | Miles et al. |
| 2012/0238893 A1 | 9/2012 | Farquhar et al. |
| 2012/0245432 A1 | 9/2012 | Karpowicz et al. |
| 2012/0265021 A1 | 10/2012 | Nottmeier |
| 2012/0283521 A1 | 11/2012 | Smith et al. |
| 2012/0330106 A1 | 12/2012 | Wright et al. |
| 2013/0046147 A1 | 2/2013 | Nichter et al. |
| 2013/0123581 A1 | 5/2013 | Fritzinger et al. |
| 2013/0158359 A1 | 6/2013 | Predick et al. |
| 2013/0245383 A1 | 9/2013 | Friedrich et al. |
| 2013/0261401 A1 | 10/2013 | Hawkins et al. |
| 2013/0261402 A1 | 10/2013 | Hawkins et al. |
| 2013/0303859 A1 | 11/2013 | Nowak et al. |
| 2013/0345520 A1 | 12/2013 | Hamada |
| 2014/0024900 A1 | 1/2014 | Capote et al. |
| 2014/0066718 A1 | 3/2014 | Fiechter et al. |
| 2014/0066941 A1 | 3/2014 | Mignucci et al. |
| 2019/0133434 A1 | 5/2019 | Lee et al. |
| 2019/0142480 A1 | 5/2019 | Woolley et al. |
| 2019/0192130 A1 | 6/2019 | Miles et al. |
| 2019/0223854 A1 | 7/2019 | Baudouin |
| 2019/0254650 A1 | 8/2019 | Martinelli |
| 2019/0328378 A1 | 10/2019 | Miles et al. |
| 2023/0149007 A1* | 5/2023 | Williams ............... A61B 17/02 600/213 |

FOREIGN PATENT DOCUMENTS

| | | |
|---|---|---|
| EP | 1192905 | 11/2010 |
| FR | 2788958 | 8/2000 |
| GB | 1520832 | 8/1978 |
| JP | 10277043 A | 10/1998 |
| WO | 9838921 | 9/1998 |
| WO | 2012093368 A1 | 10/2012 |
| WO | 2013000105 A1 | 1/2013 |

OTHER PUBLICATIONS

International Search Report for PCT/US2012/051480, ISA, dated Oct. 29, 2012.

* cited by examiner

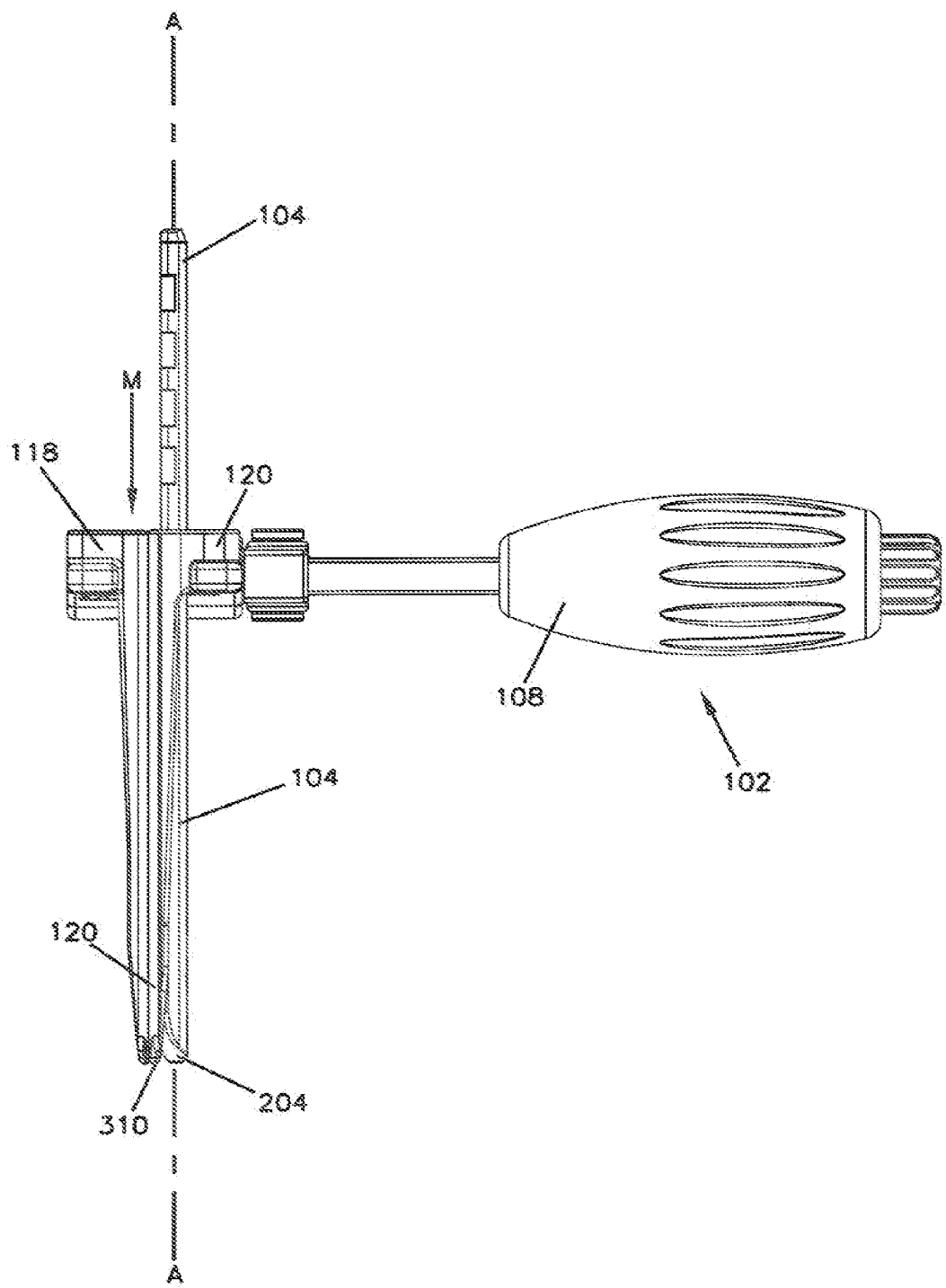

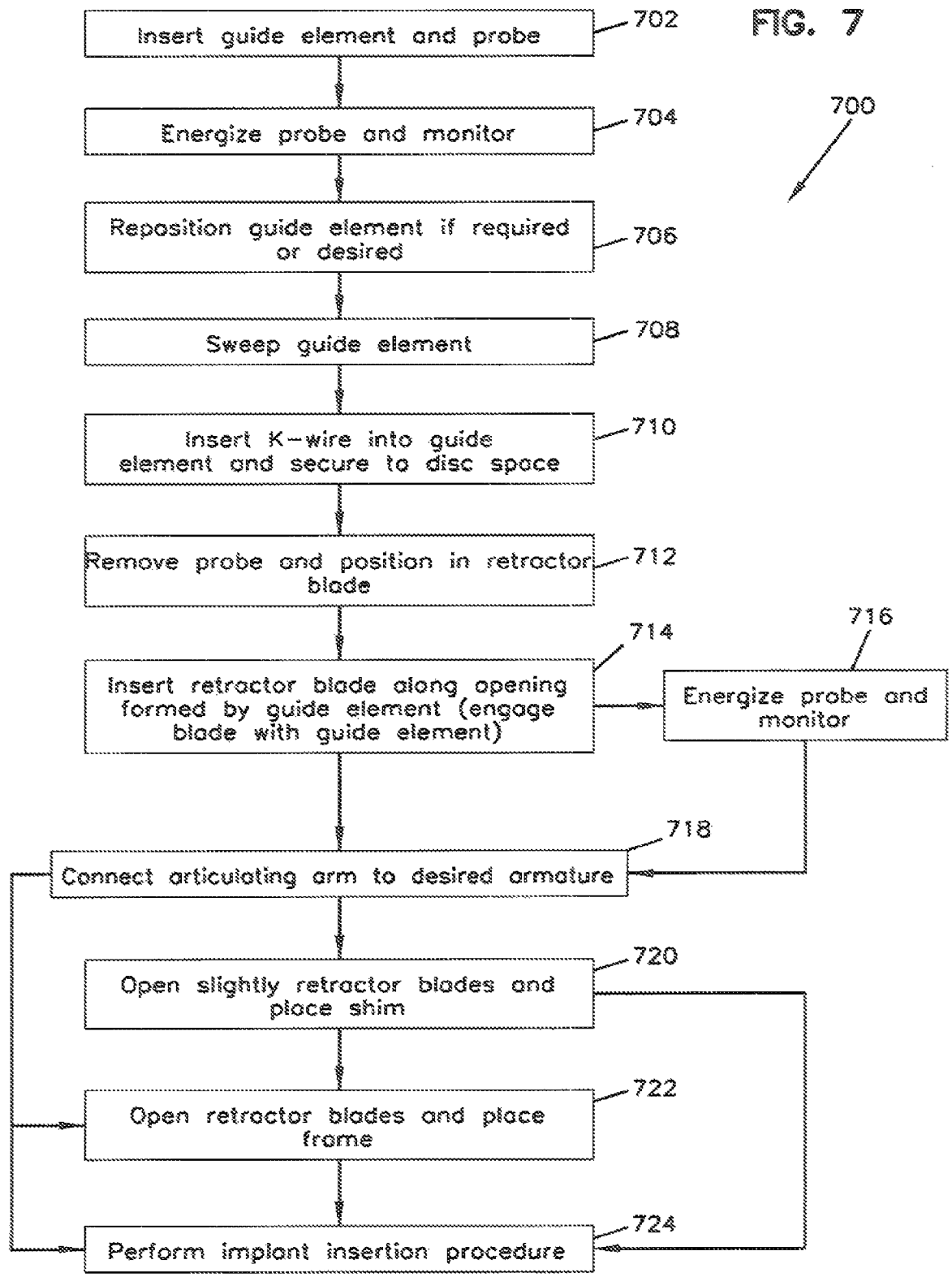

SURGICAL RETRACTOR SYSTEM AND METHODS OF USE

CROSS-REFERENCE TO RELATED APPLICATIONS

This application claims priority to and the benefit of U.S. Provisional Application Ser. No. 61/525,646, filed Aug. 19, 2011, entitled, "Surgical Retractor System and Methods of Use"; and U.S. Provisional Application Ser. No. 61/532,751, filed Sep. 9, 2011, entitled, "Surgical Retractor System and Methods of Use"; the disclosures of which are hereby incorporated by reference herein in their entireties.

INTRODUCTION

Current retractor systems for lateral spine surgical procedures create a round opening through the psoas muscle, which includes muscle fibers running mostly in the cranial-caudal direction. These systems use sequentially inserted round dilators which dilate the surgical site radially away from the initial dilator/K-wire insertion point, which can lead to compression of nerves and blood supply on the transverse process of the vertebral body. Existing retractor systems include the ability to monitor the most posterior point of each instrument being entered into the psoas, but continue to introduce larger instruments into the area of concern. These previous systems also typically include two, three, or four round dilators that must first be forced into the muscle tissue before the retractor can be inserted around the largest dilator. These round dilators, coupled with multi-blade retractors that spread radially, can cause significant muscular trauma, and can further stretch or compress nerve roots in the surrounding tissue.

SUMMARY

In one aspect, the technology relates to surgical retractors and methods of use. In one embodiment, a surgical retractor includes an elongate element defining an operational axis. A first blade, having a first blade face, is secured to the elongate element. A second blade defining an opening is moveably secured to the elongate element and defines a reference point thereon. Movement of the second blade moves the reference point in a linear direction generally parallel to the operational axis and generally orthogonal to the blade face. A guide element is removably received within the opening.

In another embodiment, a method of performing spinal surgery using a lateral approach includes inserting a guide element into a first location above a target surgical site, and repositioning the guide element into a second location above the target surgical site. The second location may be more posterior than the first location. The method includes inserting a retractor device along the guide element, with the retractor device having first and second retractor blades that are inserted along only a first side of the guide element. The first retractor blade is anchored to the target surgical site. The method includes separating the first and second retractor blades by moving the second retractor blade away from the first retractor blade, and locking the first and second retractor blades to maintain an open access to the target surgical site.

It is to be understood that both the foregoing general description and the following detailed description are exemplary and explanatory and are intended to provide further explanation of the technology as claimed.

BRIEF DESCRIPTION OF THE DRAWINGS

There are shown in the drawings, embodiments which are presently preferred, it being understood, however, that the technology is not limited to the precise arrangements and instrumentalities shown.

FIGS. 3A and 3B depict a top view and a side view, respectively, a retractor device.

FIG. 7 depicts a method of using a retractor system.

DETAILED DESCRIPTION

Figure 1:
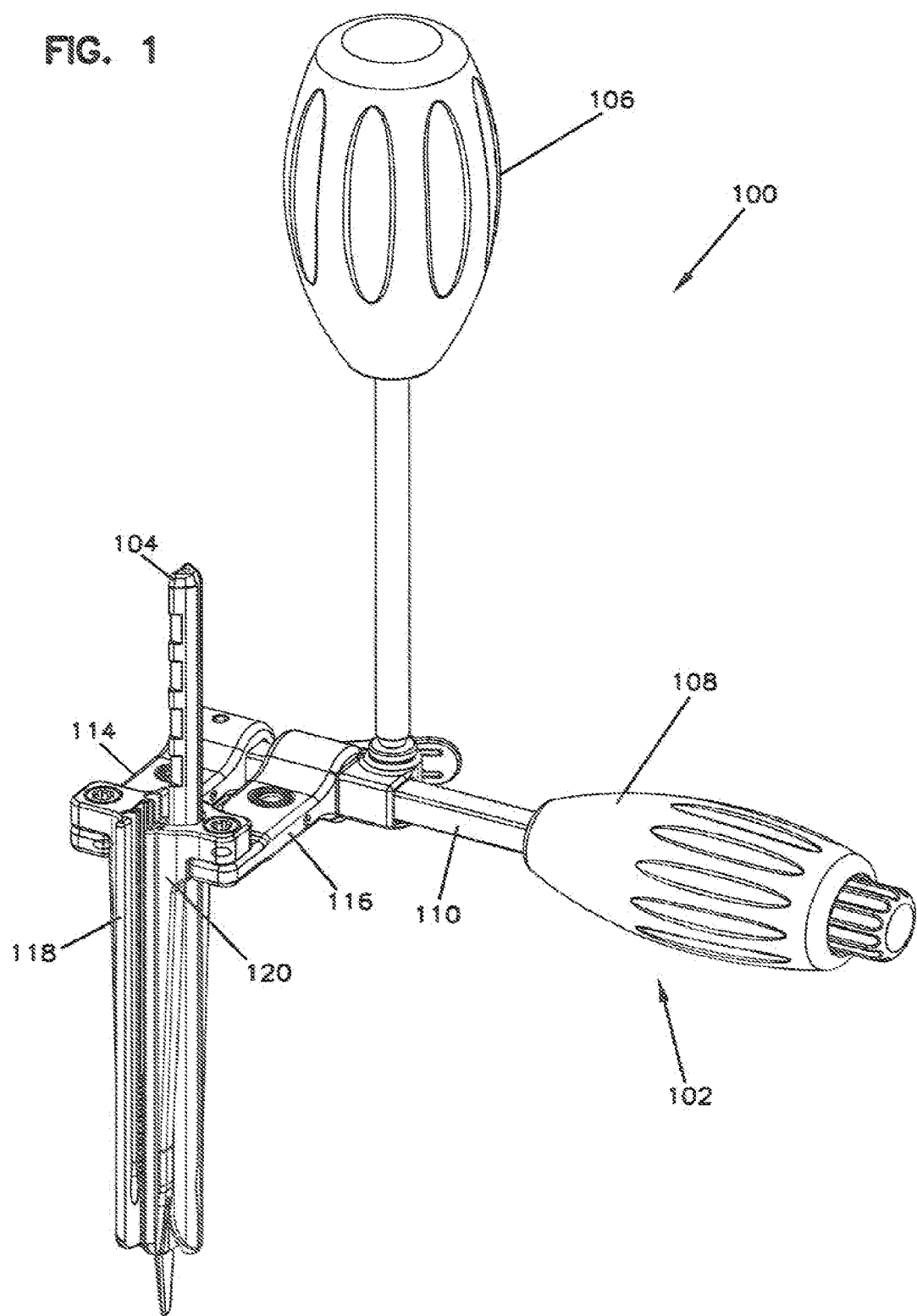
FIG. 1 depicts a perspective view of a retractor system.

FIG. 1 depicts a retractor system 100 that includes, generally, a retractor device 102, a guide element 104, and a driver 106. The retractor device 102 includes a handle 108 coupled to an elongate element 110 to which two blades 118, 120 are secured. In some embodiments, the handle 108 is a removable handle that is selectively coupled to or removed from the elongate element 110. The blades 118, 120 may be secured directly to the elongate element 110 or secured with one or more armatures 114, 116. As shown in FIG. 1, in one embodiment, the armatures 114, 116 extend from a side of the elongate element 110, such that a surgical opening created by the blades 118, 120 may be accessible by the surgeon performing the operation without obstruction by the elongate element 110. One or both of the armatures 114, 116 may be movably secured to the elongate element 110. In this particular embodiment, the driver 106 is used to actuate a moving mechanism, in this case, to rotate a gear that engages with a rack along the elongate element 110. Actuation of the moving mechanism can operate to separate the armatures 114, 116, and thus separate the blades 118, 120. This mechanism is more clearly depicted in FIG. 3B. Other moving mechanisms may be used to move the blades 118, 120 relative to the elongated elements. For example, lead screw/nut mechanisms and linear rail/slide mechanisms may be used. Certain of these systems may require additional locking elements, as described below. One of the retractor blades 118, 120 (in one embodiment, the posterior blade 120) defines an opening for receipt of the elongate guide element 104, the use of which is described below. Additionally, one or both of the blades 118, 120 may be configured to removably receive one or more shims.

Figure 2:
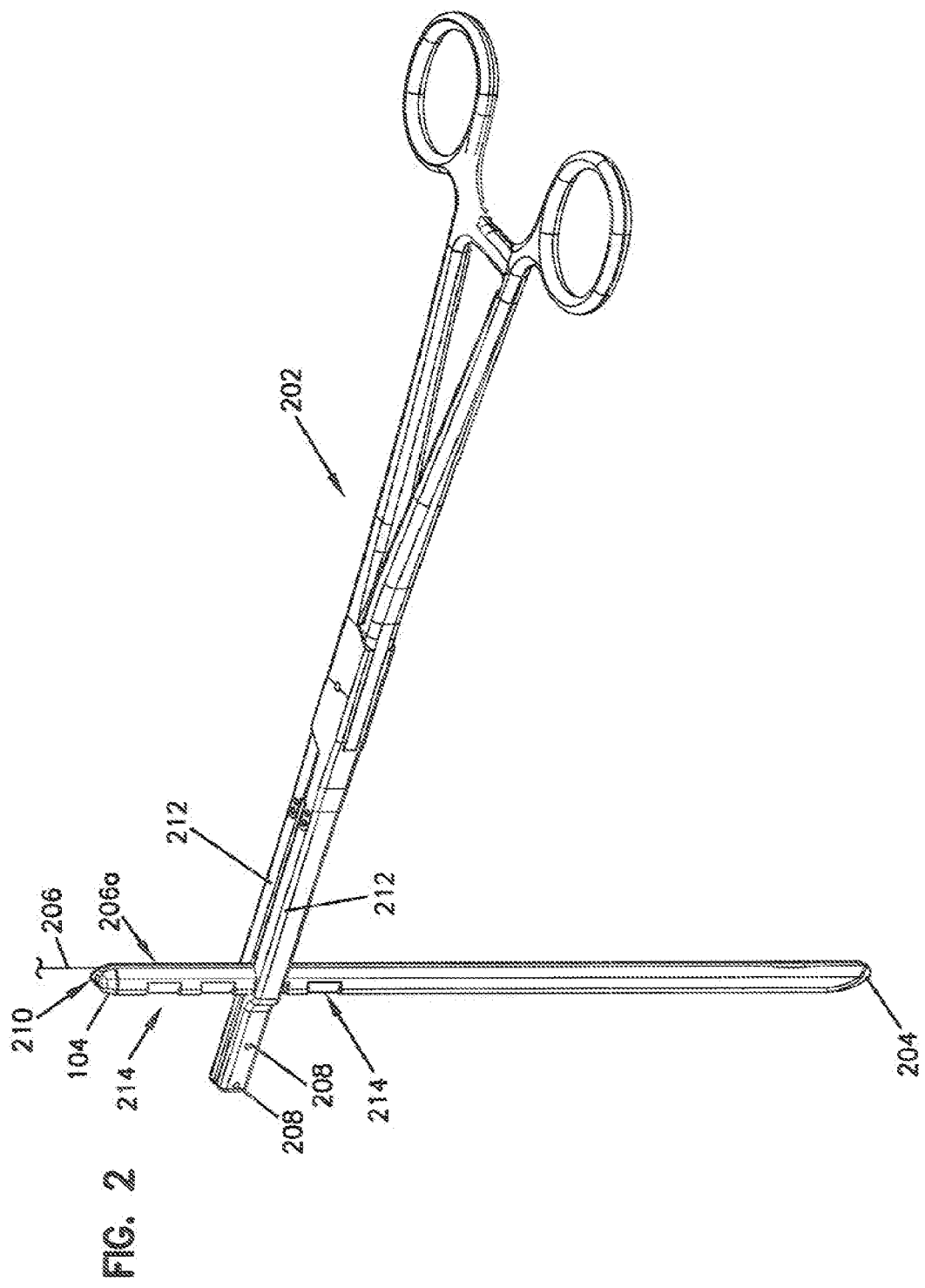
FIG. 2 depicts perspective views of a guide element insertion device.

The guide element 104 and a guide element insertion device 202 are depicted in FIG. 2. In the depicted embodiment, the guide element 104 is an elongate dissector having a generally D-shaped profile, although the present disclosure contemplates other elongated dissector profile shapes, including elliptical, trapezoidal, oblong, triangular, and the like. The blunt tip 204 and profile shape of the guide element 104 simplifies the insertion process and also assists in splitting the psoas along the plane of the muscle fibers. A probe 206 may be placed in a channel 206a or opening extending lengthwise along the guide element 104. After insertion, once a desired position is confirmed, a K-wire can be placed via the same or a second channel to dock the guide element 104 to the disc space. In an alternative embodiment, the K-wire may be already inserted into the guide element 104, prior to the guide element 104 being inserted. An opening, bore, or channel 210 in the guide element 104 sized to receive the K-wire, and discrete from the probe channel, is depicted in FIG. 2. This opening 210 may be a fully closed channel, a partially closed channel, or some combination thereof. Depending on the embodiment, the K-wire channel 210 may be located in or on the guide element 104 (as shown), in armature 114 or armature 116, or in an anterior retractor blade 118 or a posterior retractor blade 120.

The guide element 104 may include a number of notches 214 that provide an engagement surface for an insertion device 202. In the depicted embodiment, forceps including radio-lucent arms 212 are used for insertion. Other types of insertion devices may be used, or the guide element 104 may also be positioned by hand, if desired. The radio-lucent forceps arms 212 typically will not show during fluoroscopy, but radio-opaque markers 208 may be included on the arms 202 to assist in positioning. Radio-opaque markers 208 placed at other locations indicating the positions/locations of certain elements may be utilized. Additionally, the guide element 104 may also be radio-lucent. Radio-opaque markers also may be positioned proximate the center and anterior border of an implant to be inserted during the surgical procedure.

Figure 3B:
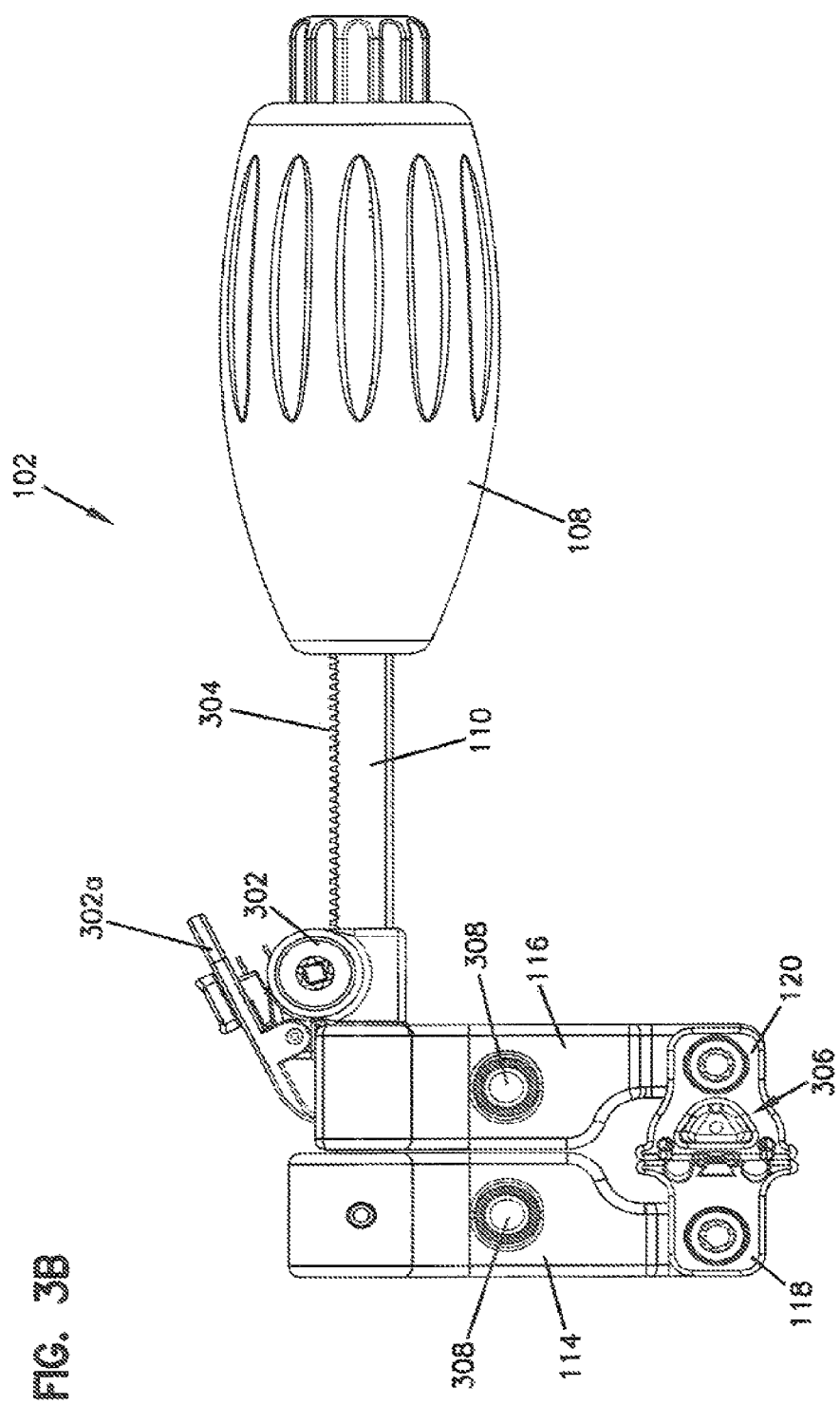

FIGS. 3A-3B depict various views of a dissector-type guide element 104 used in conjunction with a retractor device 102. As initially described above, the driver is used to actuate a moving mechanism, in this case, to rotate a gear 302 that engages with a rack 304 along the elongate element 110. A locking element 302a a may prevent further movement of the gear when engaged, by for example, engaging the rack 304. The guide element 104 is received within an opening 306 defined by at least one of the retractor blades 118, 120. In the depicted embodiment, the opening 306 is located in the posterior blade 120. Alternatively or additionally, an opening 306 may be located in the anterior blade 118 or in either or both of the armatures 114, 116. Once the guide element 104 is inserted into the skin surface and muscle tissue to a desired depth, the retractor device 102 is moved M along an axis A so as to receive the guide element 104 in the opening 306. As most readily seen in FIG. 38, the flat portion of the generally D-shaped guide element 104 is facing anteriorly (i.e., towards the blades 118, 120), such that the retractor device 102 is slid over the guide element 104 with the face surfaces of the opposing retractor blades 118, 120 facing each other. Since the guide element 104 is located in the opening 306 defined in the exterior surface of the posterior blade 120, all or substantially all of both blades 118, 120 are located on the same side of the guide element 104, unlike dilator/retractor systems that locate the blades 118, 120 on both sides of (or around) dilators. FIG. 3A depicts a distal end 310 of the posterior retractor blade 120, along with the guide element 104 located along a rear surface of the blade 120. In general, the distal ends 310 of the retractor blades 118, 120 should not be inserted lower than the tip 204 of the guide element 104, but the blades 118, 120 may be inserted further, if desired.

FIG. 3B also depicts the retractor lock 302a, which is used to fix the position of the posterior blade armature 116 along the elongate element 110 and to prevent inadvertent movement of the armature 116, and therefore the blade 120, along the elongate element 110. In this case, the retractor lock 302a may be disengaged prior to rotating the gear 302 with the driver 106, as described above in the context of FIG. 1. The retractor lock 302a then may be reengaged to prevent further movement of the armature 116. The retractor lock 302a may engage with the elongate element 110, either at the rack 304 itself or at a separate point located on the elongate element 110. Each armature 114, 116 includes an articulating arm connection 308, such as that described below. Once the retractor blades 118, 120 are inserted into the psoas muscle, an articulating arm (not shown) may be connected to either the anterior blade armature 114 or the posterior blade armature 116. An opposite end of the articulating arm is connected to a fixed point (typically on the operating table), to hold the retractor device 102 in position during operation of the opening mechanism. When the articulating arm is connected to the anterior blade armature 114, actuation of the opening mechanism will move the posterior blade 120 along the elongate element 110, towards the handle 108. When the articulating arm is connected to the posterior blade armature 116, actuation of the opening mechanism will move the anterior blade 118 in a direction away from the posterior blade 120. Note that in this second configuration, since the posterior blade armature 116 is connected to the elongate element 110, each of the anterior blade 118, its armature 114, the elongate element 110, and the handle 108 move relative to the fixed posterior blade 120 as the opening mechanism is operated. Depending on the location of the guide element 104 and desired position of the surgical corridor, an operator may make the articulating arm connection 308 as desired. It should be noted that by fixing the position of the posterior blade 120 with the articulating arm, the possibility of compressing nerves and/or restricting the blood flow due to pressure on the transverse process is reduced or eliminated. The two-blade, flat-blade design assists in splitting the psoas muscle along the plane of the muscle fibers, thereby reducing trauma.

It should also be noted that either or both of the blades 118, 120 may be configured with any number of openings, channels, or other structures that allow for receipt of an electrode probe, such that the location of nerves may be determined during insertion of the retractor device 102, during opening of the blades 118, 120, or after opening of the blades 118, 120. Use of such probes for identifying nerve proximity and direction is well-known within the field of spinal surgery, and will not be further described herein. Additionally, the same or other channels may be used to hold a light source used to illuminate the surgical corridor.

Figure 4:
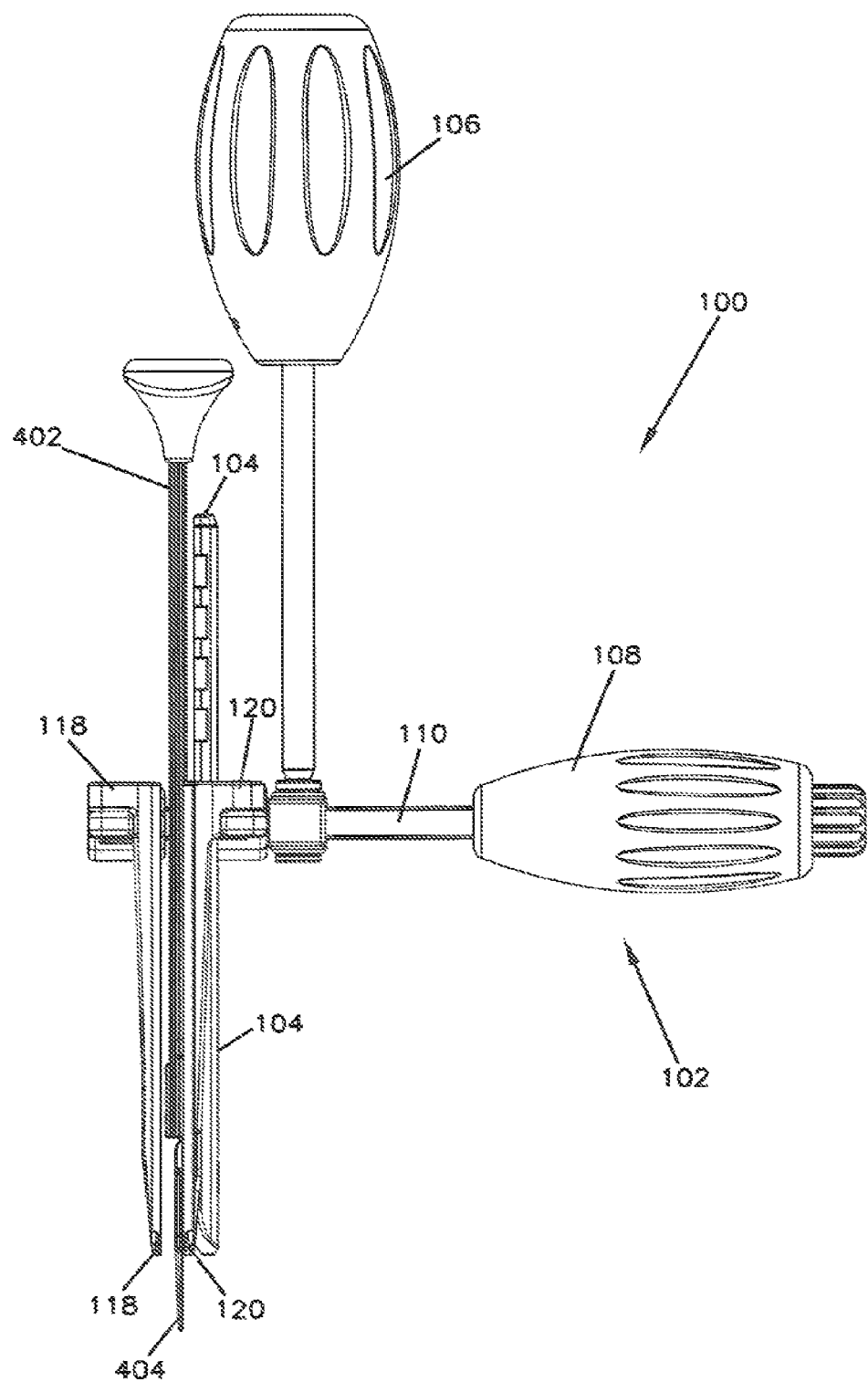
FIG. 4 depicts a side view of a retractor system.
Figure 5B:
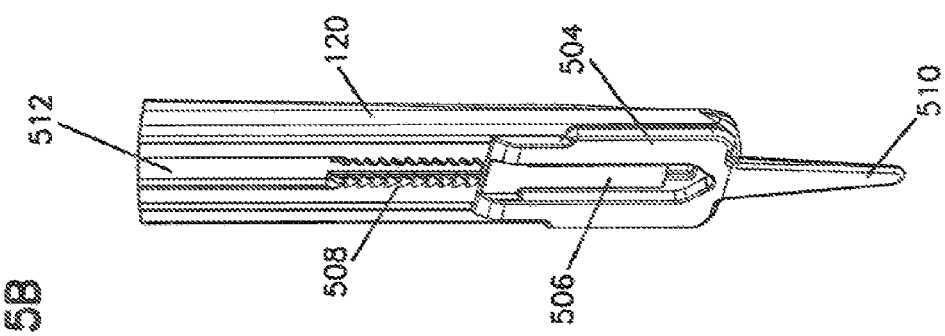
FIGS. 5A and 5B depict enlarged partial perspective views of a retractor blades.
Figure 5A:
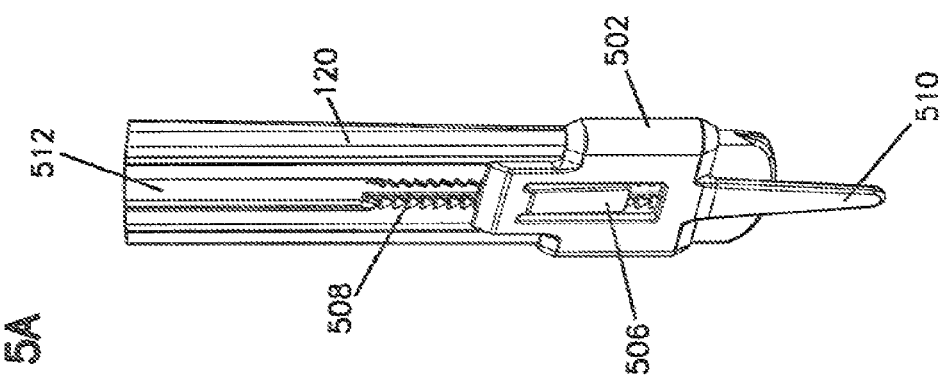

FIG. 4 depicts a partial side view of the retractor system 100. In some embodiments, the retractor blades 118, 120 of the device may be fitted with one or more shims that serve particular purposes during surgery. Widening shims may be used to help ensure muscle tissue does not encroach on the surgical corridor. Lengthening shims may be used to effectively lengthen the depth of penetration of the blades 118, 120. Intradiscal shims may be used to penetrate the disc space of the spine so as to access the disc and hold one of the blades 118, 120 of the retractor device 102 in place, relative to the spine. As depicted in FIG. 4, the anterior blade 118 and the posterior blade 120 may be separated slightly so as to allow access to the space between with a shim inserter 402, which is used to guide a shim 404 down to the appropriate location along the blade. FIGS. 5A and 5B depict a wrap-around shim 502 and an internally-confined shim 504, respectively. Either shim 122 type may be used in conjunction with the retractor device 102, on either or both of the anterior blade 118 and the posterior blade 120. Once the shim(s) are installed, it may be desirable to remove either or both of the K-wire and the guide element 104 prior to opening the retractor blades 118, 120 to the desired maximum position. Either shim 502, 504 may include a ratchet 506 that engages with a rack 508 located on the blade 120, such that the shim 502, 504 may be inserted to a desired depth and held in place. Both of the shims 502, 504 depicted in FIGS. 5A and 5B are intradiscal shims that include a tip 510 that may be inserted into the disc space, to help fix the location of the blade 120 internal to the body. The rack 508 may extend along a portion of an inner channel 512 of the blade 118, 120, or may extend the entire length of the inner channel 512.

Figure 6A:
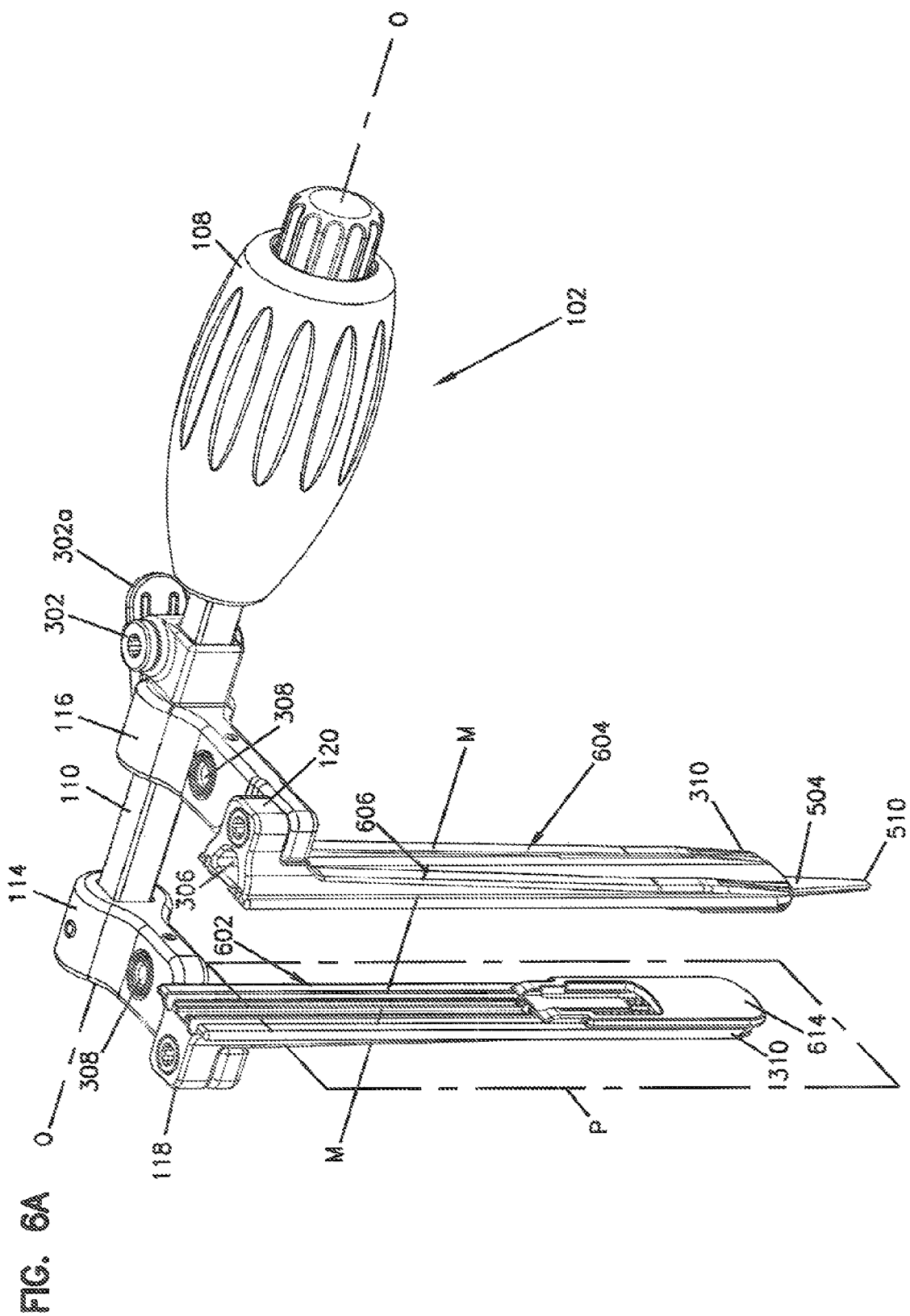
FIGS. 6A and 6B depict perspective views of a retractor device.
Figure 6B:
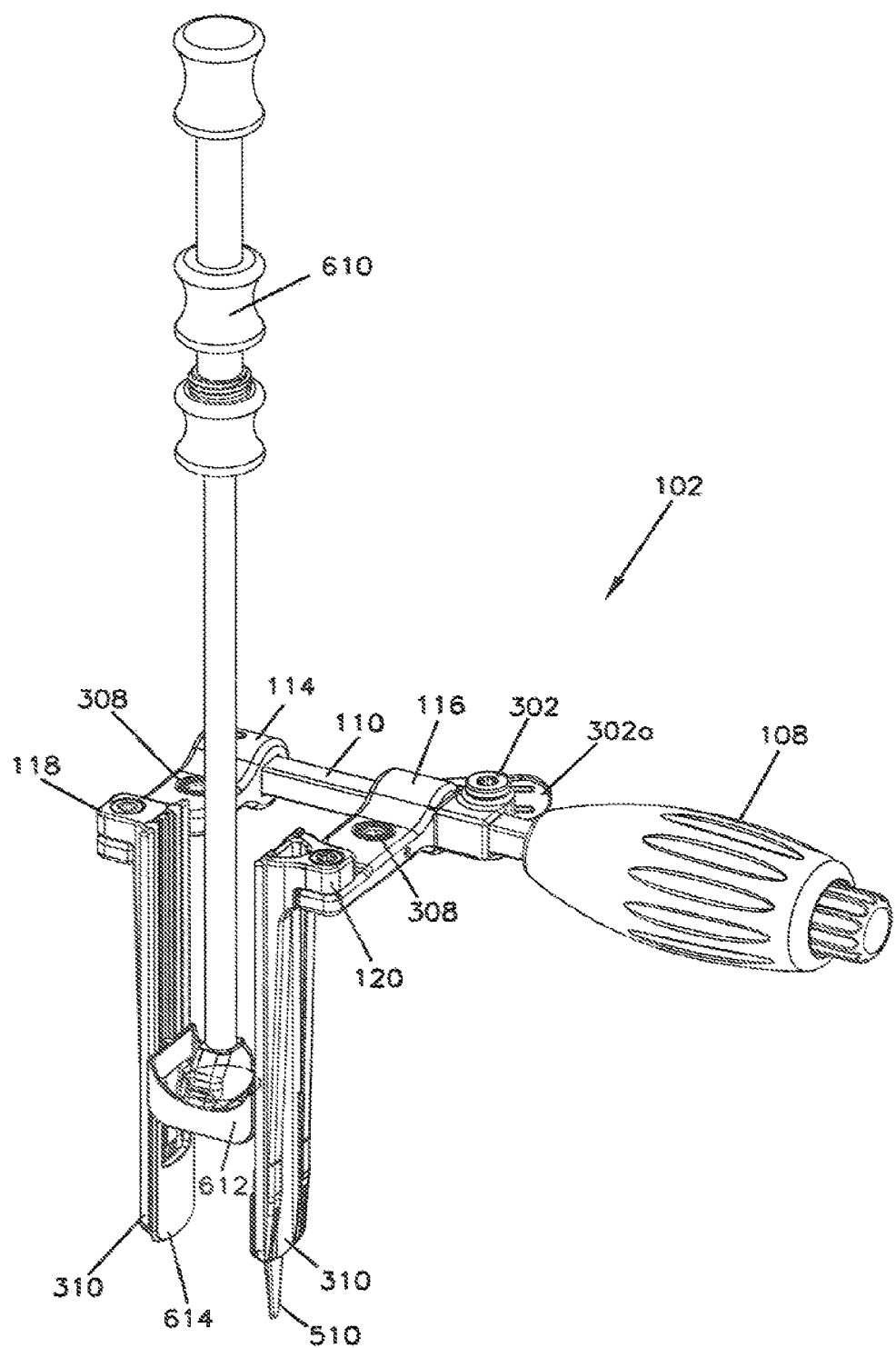

FIGS. 6A-6B depict the embodiment of the retractor device 102 shown in an open position, creating a surgical corridor within the muscle tissue. Of course, a functional surgical corridor need not require the blades 118, 120 to be opened to a maximum distance. If desired or required, a frame 612 may be placed between the blades 118, 120 to provide support to the distal ends 310 of the blades 118, 120. This may be useful, for example, should the surrounding tissue force an inward deflection of the blade ends 310 and thus cause a narrowing of the surgical corridor. The frame 612 may be held in place via the inner channels 512 located in either or both of the blades 118, 120, and may be inserted with an insertion element 610 (e.g., a pair of forceps). FIGS. 6A and 6B also depict a lengthening shim 614 located on the anterior blade 118.

Movement of the blade relative to the elongate element 110 is described with reference to FIG. 6A. The elongate element 110 defines an operational axis O. Each front face of the anterior blade 118 and the posterior blade 120 define a plane. For clarity, only anterior plane P is depicted in FIG. 6A. Each of the blades 118, 120 also includes a reference point 606 located thereon. The reference point 606 may be located on the face surface 602 or rear surface 604 of the blade, or may be a defined point thereon, for example, a center of gravity, a blade tip, a radio-opaque reference point, etc. Additionally, the reference point 606 need not be a distinct physical point. Instead, that term is used herein to further define movement of the blades 118, 120. Regardless, a predetermined reference point 606 is identified on the rear surface 604 of the posterior blade 120 in FIG. 6A. For the purposes of this example, the articulating arm described above is connected to the anterior blade armature 114. Therefore, as the moving mechanism (the gear 302) is operated, the posterior blade 120 moves toward the handle 108. In that regard, the reference point 606 moves along an axis of movement M that is generally parallel to the operational axis O and generally orthogonal to the anterior blade plane P. This configuration of axes and planes, as well as the substantially flat configuration of the blades 118, 120, helps ensure muscular separation along the muscle fiber plane, thereby limiting muscular trauma. Of course, if the articulating arm is connected to the posterior blade armature 116, similar movement of the anterior blade 118 occurs. A reference point located on the anterior blade 118 moves along an axis generally parallel to the operational axis O, as well as generally orthogonal to the posterior blade plane. Also, if the articulating arm is connected to the posterior blade armature 116, the intradiscal shim 504 depicted may be inserted into the intradiscal space to help further limit movement of the posterior blade 120. In general, the tip 510 of the intradiscal shim 504 is not extended beyond the blade tip 310 during movement of the blade 118, 120 on which the intradiscal shim 504 is installed.

FIG. 7 depicts a method 700 of using a retractor system in a surgical procedure. Although the method is described in the context of lateral-approach spinal surgery, it should be noted that the systems and methods described herein may be used in virtually any surgery where limited muscular and/or nerve trauma is desired. In surgeries where limited, controlled separation of muscle fibers is desirable, the retractor system described herein may be particularly advantageous.

Further, while shown in FIG. 7 as a series of operations, method 700 can combine operations or eliminate operations altogether. For example, operations related to nerve monitoring and probes may be omitted in the event the surgeon does not elect to use nerve monitoring. Initially, a guide element is inserted (operation 702) into the area of interest (in this case, the psoas muscle) and directed toward the target tissue, organ, or skeletal structure (in this case a vertebrae or disc space). An electrode probe may be located in the guide element prior to insertion and introduced at the same time as the guide element. The probe may then be energized and the feedback monitored (operation 704) to check for nerve response (e.g., in the lumbar plexus). In certain surgeries, the guide element is positioned so as to be centered near the anterior one-third of the intravertebral disc. The guide element may be repositioned (operation 706) as required or desired, generally until a suitable location is found. Electrode monitoring (operation 704) may be repeated to confirm the location is safe for the surgery to continue. In a particular embodiment, the guide element is repositioned (operation 706) posteriorly in small increments until the desired location is found and nerve monitoring indicates the location is safe for surgery to continue. In a particular embodiment, the guide element is positioned as far posterior as possible, so that subsequent retractor blade movement will be a movement of only the anterior blade away from the posterior blade.

Once the proper position is confirmed, the guide element may be swept (operation 708) side-to-side so as to create a plane in the psoas muscle and make an initial opening into which a retractor device will be inserted. Thereafter, a K-wire may be inserted (operation 710) via the guide element toward the target region, and secured relative to the disc space. Prior to insertion of the retractor device, the monitoring probe may be removed (operation 712) from the guide element and inserted into one of the retractor blades. This would allow for monitoring of nerve response during insertion of the retractor, which may be desirable in certain situations. Alternatively, a second monitoring probe may be used with the retractor. Due to the unique configuration of the retractor system, the retractor blades are inserted on the same side of the guide element, into the opening formed by the earlier sweeping movement thereof. As described above, this helps separate the psoas muscle along the muscle fibers. Additionally, by inserting both blades on the same side of the guide element, the guide element can be positioned on the posterior side of the desired surgical site, with the posterior blade also being positioned on the posterior side of the desired surgical site.

As the retractor device is inserted (operation 714) into the initial surgical opening, the guide element is inserted into the opening defined by the retractor blade, typically the posterior retractor blade. After inserting the retractor blade a certain distance into the muscle, the probe may be energized and the feedback monitored to confirm location and/or proximity of the blades relative to nearby nerves (operation 716). This blade position monitoring operation 716 need not be performed however. Regardless, once the retractor blades reach their desired depth of penetration, an articulating arm may be connected (operation 718) to either of the posterior blade armature and the anterior blade armature. As described above, connection to either of the armatures will dictate which of the armatures moves and, accordingly, the direction of separation of the retractor blades, (i.e., anteriorly or posteriorly). Once secured to the armature, a number of different actions may be taken in virtually any order to complete the surgical procedure. For example, the blades may be spread slightly and a shim may be inserted (operation 720). A shim may accomplish any of the purposes described above, and in one embodiment is used to further anchor the distal end of one of the blades to help secure it place relative to a desired surgical site. Thereafter or alternatively, the blades may be spread further and a frame may be inserted (operation 722) to provide rigidity to the distal ends of the retractor blades. Again, this blade separation may occur from just a single blade moving while the other blade remains generally in place. At any point, desired surgical procedures may be performed (operation 724), such as a partial or full discectomy, and insertion of an implant per the surgeon's discretion. Of course, surgical procedures may be performed at any time after insertion of the blades, and the shims and/or the frame may be inserted at any time during the procedure, as required. For example, if a surgical procedure is initiated without insertion of a frame, but during the procedure, the surgical corridor begins to contract, the surgeon may then insert the shim and/or the frame. Additionally, the looking mechanism may be locked and unlocked as required during the procedure.

Materials utilized in the manufacture of the retractor system may be those typically used in surgical equipment. Stainless steel, titanium, and other robust metals that may be sterilized may be used. In applications where fluoroscopy is desirable or required during the procedure (e.g., in the spinal surgery procedures described herein), radio-lucent materials may be particularly desirable. In those applications, aluminum, anodized aluminum, and rigid polymers may be utilized. Carbon fiber-reinforced polymers may be particular useful, as they are lightweight, extremely strong, and may be sterilized. Of course, retractor systems utilizing a combination of materials may be used. For example, radio-lucent materials may be used for the blades and less expensive radio-opaque material may be utilized for the elongate element and armatures. Additionally, radio-lucent materials may be impregnated in discrete locations with radio-opaque materials such that position of certain parts of the system may be visible during procedures, without impeding overall visibility.

While there have been described herein what are to be considered exemplary and preferred embodiments of the present technology, other modifications of the technology will become apparent to those skilled in the art from the teachings herein. The particular methods of manufacture and geometries disclosed herein are exemplary in nature and are not to be considered limiting. It is therefore desired to be secured in the appended claims all such modifications as fall within the spirit and scope of the technology. Accordingly, what is desired to be secured by Letters Patent is the technology as defined and differentiated in the following claims, and all equivalents.

What is claimed is:

1. A surgical retractor comprising:
    an elongate element defining an elongate element distal end and an elongate element proximal end with a length therebetween, the elongate element defining an operational axis along the length thereof, wherein the elongate element includes:
        a rack;
    a first blade having:
        a first upper portion secured to the elongate element distal end; and
        a first blade portion comprising a first blade face; and
    a second blade arm movable along the elongate element, the second blade arm having:
        a first end;
        a second end;
        an opening extending entirely through the second blade arm proximate the first end and through which the elongate element extends;
        an articulating arm connector positioned between the opening and the second end, the articulating arm connector configured to fix the position of the second blade arm with respect to an operating table by connecting with a first end of an articulating arm having a second end connected to an operating table; and
        a gear mechanism disposed to cooperate with the rack to move the position of the second blade arm along the length of the elongate element;
    a second blade having:
        a second upper portion secured to the second blade arm; and
        a second blade portion having a second blade face that faces the first blade face, wherein the second blade arm is positioned along the length of the elongate element at a position between the elongate element proximal end and the first blade, the second blade arm being configured to move along the length of the elongate element,
    wherein the first blade defines a first reference point located thereon;
    wherein the second blade defines a second reference point located thereon;
    wherein an axis of movement is defined through the first reference point and the second reference point that is parallel to the operational axis;
    wherein a movement of the position of the second blade arm along the length of the elongate element moves one or both of the first reference point and the second reference point in a linear direction along the axis of movement and orthogonal to the second blade face; and
    wherein a plane bisecting the articulating arm connector extends through a central portion of the second blade arm and through the second blade.

2. The surgical retractor of claim 1, further comprising a lock configured to prevent movement by engaging with the rack.

3. The surgical retractor of claim 1, further comprising:
    a guide received in an opening, wherein the guide is located along a second blade exterior surface.

4. The surgical retractor of claim 3, wherein the guide comprises a dissector.

5. The surgical retractor of claim 1,
    wherein one or both of the first blade and the second blade define a channel; and
    wherein the channel is configured to receive at least partially at least one of a shim, a K-wire, a light source, a probe, and a support frame.

6. The surgical retractor of claim 1, further comprising:
    a driver engaged with the gear and having a driver length positioned orthogonal to the operational axis, wherein rotation of a driver handle about a driver handle axis activates movement of the second blade.

7. The surgical retractor of claim 1,
    wherein the length of the elongate element is orthogonal to the first blade face;
    wherein a length of the second blade arm is orthogonal to the length of the elongate element; and
    wherein a length of the second blade arm is parallel to the length of the first blade face.

8. The surgical retractor of claim 1, further comprising: an electrode probe configured to facilitate location of nerves during insertion of the surgical retractor.

9. The surgical retractor of claim 1, wherein the surgical retractor is configured to be inserted through a psoas muscle.

10. The surgical retractor of claim 1, further comprising: a first blade arm extending from the elongate element to the first blade, the first blade arm having:
a first articulating arm connector configured to fix the position of the first blade arm with respect to the operating table by connecting the first articulating arm connector with the first end of the articulating arm and
wherein the articulating arm connector of the second blade arm is a second articulating arm connector.

11. A surgical retractor system comprising:
a surgical retractor comprising:
an elongate element comprising a rack and defining an operational axis along a length between an elongate element distal end and an elongate element proximal end;
a first blade having a first upper portion secured to the elongate element distal end and a first blade portion comprising a first blade face, wherein the first blade defines a first reference point;
an arm movable along the elongate element including:
an opening extending entirely through the arm and through which the elongate element extends:
a gear positioned at a location along the length of the elongate element to cooperate with the rack to move the position of the arm along the rack; and
an articulating arm connector; and
a second blade secured to the arm and defining a second reference point,
wherein the articulating arm connector is aligned with the second blade and a plane extends through a central portion of the articulating arm connector, through a central portion of the arm, and through the second blade;
an articulating arm having a first end coupled to an operating table and a second end configured to couple to the articulating arm connector;
a driver coupled to the gear; and
wherein the gear is disposed such that rotating the gear with the driver causes movement of one or both of the reference points along an axis of movement parallel to the operational axis and orthogonal to the first blade face.

12. The surgical retractor system of claim 11, wherein a length of the driver is orthogonal to the operational axis.

13. The surgical retractor system of claim 11, further comprising:
a lock of the surgical retractor configured to resist movement of the position of the arm along the length of the elongate element.

14. The surgical retractor system of claim 11, further comprising:
a guide configured to be inserted into an area of interest in a patient through a psoas muscle of the patient,
wherein the surgical retractor is configured to be inserted along the guide to the area of interest.

15. The surgical retractor system of claim 11, wherein the surgical retractor further comprises:
a first blade arm extending from the elongate element to the first blade, the first blade arm having:
a first articulating arm connector configured to fix the position of the first blade arm with respect to the operating table by connecting the first articulating arm connector with the second end of the articulating arm; and
wherein the arm is a second blade arm and the articulating arm connector of the arm is a second articulating arm connector.

16. A system comprising:
a surgical retractor comprising:
an elongate element comprising a rack and defining an elongate element distal end and an elongate element proximal end with a length therebetween, the elongate element defining an operational axis along the length thereof;
a first blade having a first upper portion secured to the elongate element distal end and a first blade portion comprising a first blade face;
an arm movable along the elongate element, the arm having:
a first end;
a second end
an opening extending entirely through the arm and through which the elongate element extends:
an articulating arm connector located between the first end of the arm and the second end of the arm; and
a gear mechanism disposed to cooperate with the rack to move the position of the arm along the length of the elongate element;
a second blade having:
a second upper portion secured to the arm; and
a second blade portion having a second blade face that faces the first blade face,
wherein the articulating arm connector is aligned with the second blade, and
wherein the arm is positioned along the length of the elongate element at a position between the elongate element proximal end and the first blade, the arm being configured to move along the length of the elongate element;
an articulating arm having a first end coupled to an operating table and a second end coupled to the articulating arm connector; and
a locking element configured to resist movement by engaging with the rack;
wherein the gear mechanism and the rack cooperate to form a rack-and-gear mechanism configured to modify the position of the arm along the elongate element;
wherein modification of the position of the arm along the length of the elongate element causes movement of one or both of the blades along an axis of movement parallel to the operational axis and orthogonal to the second blade face;
wherein the length of the elongate element is orthogonal to the first blade face;
wherein a length of the arm is orthogonal to the length of the elongate element; and
wherein a length of the arm is parallel to the length of the first blade face; and
wherein a plane bisecting the articulating arm connector extends through a central portion of the arm and through the second blade.

17. The system of claim 16, further comprising:
a guide element; and
a driver engaged with the gear and extending orthogonal to the operational axis.

18. The system of claim 16, wherein the surgical retractor further comprises:
- a second articulating arm connector at a fixed location relative to the elongate element and configured to couple to the articulating arm; and
- wherein the articulating arm connector of the arm movable along the elongate element is a first articulating arm connector.

* * * * *